United States Patent
Buckman et al.

(10) Patent No.: US 7,022,094 B2
(45) Date of Patent: Apr. 4, 2006

(54) SPLINT SYSTEM AND METHOD OF USE

(75) Inventors: Robert F. Buckman, Radnor, PA (US); Jay A. Lenker, Laguna Beach, CA (US); Donald J. Kolehmainen, Laguna Niguel, CA (US)

(73) Assignee: Damage Control Surgical Technologies, Inc., Laguna Beach, CA (US)

( * ) Notice: Subject to any disclaimer, the term of this patent is extended or adjusted under 35 U.S.C. 154(b) by 0 days.

(21) Appl. No.: 10/764,123

(22) Filed: Jan. 24, 2004

(65) Prior Publication Data

US 2004/0167450 A1   Aug. 26, 2004

Related U.S. Application Data

(60) Provisional application No. 60/442,453, filed on Jan. 24, 2003.

(51) Int. Cl.
*A61F 5/00* (2006.01)
(52) U.S. Cl. .............................. 602/23; 602/32; 602/36; 602/39
(58) Field of Classification Search ................. 602/23, 602/32, 33, 35, 36, 38, 39, 40; 128/869–870
See application file for complete search history.

(56) References Cited

U.S. PATENT DOCUMENTS

| | | | | |
|---|---|---|---|---|
| 2,319,400 A | * | 5/1943 | Hartmann et al. ............ | 602/40 |
| 2,604,889 A | * | 7/1952 | Erickson ....................... | 602/35 |
| 2,815,022 A | * | 12/1957 | Krumm ......................... | 602/40 |
| 4,407,277 A | * | 10/1983 | Ellison .......................... | 602/39 |
| 4,608,971 A | * | 9/1986 | Borschneck .................. | 602/23 |
| 4,649,907 A | * | 3/1987 | Whitehead et al. ........... | 602/40 |
| 5,063,918 A | * | 11/1991 | Guhl ............................. | 602/40 |
| 5,162,039 A | * | 11/1992 | Dahners ....................... | 602/23 |
| 5,217,488 A | * | 6/1993 | Wu .............................. | 606/241 |
| 5,230,700 A | * | 7/1993 | Humbert et al. .............. | 602/23 |
| 5,891,066 A | * | 4/1999 | Borschneck et al. ........... | 602/5 |
| 5,897,555 A | * | 4/1999 | Clyburn et al. ............... | 606/54 |
| 6,045,525 A | * | 4/2000 | Chitwood ..................... | 602/36 |
| 6,786,882 B1 | * | 9/2004 | Slishman ..................... | 602/36 |

* cited by examiner

*Primary Examiner*—Henry Bennett
*Assistant Examiner*—Amanda Wieker (57) ABSTRACT

Devices and methods are disclosed for achieving control and stabilization of bone fractures in mammals, most specifically humans. Stabilization and traction is often required to support fractured bones of the arms or legs. The devices and methods disclosed herein are especially useful in the emergency or military setting. The devices utilize a collapsible frame that may be expanded and locked into position. The frame is fabricated primarily from polymeric materials with low radiodensity. The limb contact regions are adjustable to fit a wide variety of limb sizes and fracture locations. The traction applied by the splint is adjustable, controllable and measurable. The traction splint of the current invention is sufficiently compact that it will fit in a compartment of most ambulances and emergency rescue vehicles, thus making it more available for use than standard traction splints in use today. The traction splint is either a separate device or integrated into a backboard.

14 Claims, 8 Drawing Sheets

SPLINT SYSTEM AND METHOD OF USE

This application claims priority benefit under 35 USC § 119(e) from U.S. Provisional Application No. 60/442,453, filed Jan. 24, 2003, entitled METHOD AND APPARATUS FOR CONTROL OF PERIPHERAL BONE FRACTURES, the entire contents of which is incorporated herein by reference.

FIELD OF THE INVENTIONS

This inventions described below relate to methods and devices for splinting fractures of bones in the arms and legs.

BACKGROUND OF THE INVENTION

Many splints and splint systems exist for applying traction to broken bones of the arms or legs. Exemplary devices include Sager Splints and Hare Traction Splints. These devices are large, heavy, cumbersome, and do not fit on helicopters and take up excessive space in ambulances. These current traction splints are fabricated from metallic components and are radiopaque. The radiopaque mass of the splint hinders radiographic or X-Ray analysis of the fracture. Also, MRI and other imaging techniques cannot be used with splints with metal components.

The current method of lower extremity bone fracture stabilization and therapy comprises placing the patient on a stretcher, litter or backboard. Diagnosis of a femur fracture triggers the application of a current traction splint as a separate procedure from placing the patient on the backboard. The placement of a traction splint involves the steps of rolling the patient away from the affected side. Next, the splint is placed so that an ischial contact bar is engaged with the ischium of the pelvis. The injured lower extremity is laid upon the cross-straps of the current traction splint. The traction splint is extended to its desired length. The foot strap is wrapped around the lower leg and is engaged against the top of the foot. The rings on the bottom of the foot strap are affixed to a hook attached to a ratcheting roller device to apply tension to the foot. Elastic straps are wrapped around the side of the leg to hold the leg in place relative to the traction splint. This process is extremely time consuming, complicated, cumbersome, and painful.

New devices and methods are needed to permit rapid fluoroscopic or X-Ray analysis of broken bones in the arms and legs while a traction splint is in place. In addition, improved devices are necessary in order to permit traction devices and splints to fit in the restricted space available on emergency vehicles. The traction splint would be even more convenient and space-efficient if it were incorporated into a backboard or gurney.

SUMMARY OF THE INVENTION

The devices and methods described below provide for initial treatment of broken bones in the arms and legs. Various traction splints fabricated primarily from non-metallic, minimally radiodense or radio-opaque components are presented. The use of non-metallic components allows the splint to be minimally radiopaque. Under X-Ray evaluation, the splints will show as a shadow but will not obscure the details of the bone in such a way as to hinder reading and analysis of the X-Ray image.

The splint structure is collapsible so as to be highly compact in its storage state. The splint may controllably be opened from its collapsed or compact state to its deployed or expanded state to support a broken arm or leg. The splint, once opened, may be locked in place to maintain a stable configuration.

The traction splint may be combined with an integral backboard or stretcher. The backboard traction splint combination relies on the backboard to provide the longitudinal support structure for offset components that affix around the broken limb to generate the traction and provide injury stabilization of that appendage. The offset components ride in slots within the backboard. The offset components can be locked down at discreet or continuously variable locations on the backboard.

DETAILED DESCRIPTION OF THE INVENTION

Figure 1A:
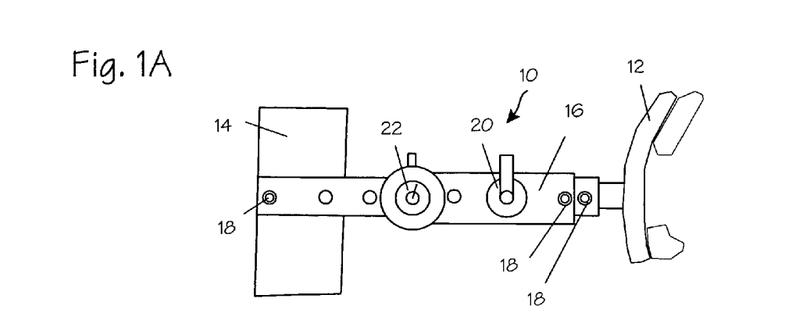
FIGS. 1A, 1B and 1C illustrate the leg traction splint.

FIG. 1A illustrates a traction splint 10 in its collapsed configuration. The traction splint 10 further comprises a distal support member 12, a proximal support member 14, an axial support 16, one or more axial support locks 18, a traction force generating mechanism 20 and a traction force measuring mechanism 22. The distal support member 12 is affixed to the axial support 16 at or near its distal end. The proximal support member 14 is affixed to the proximal end of the axial support 16. The axial support locks 18 are affixed to at least one component of the axial support 16 and selectively engage with other components of the axial support 16. The force generating mechanism 20 is affixed to the axial support 16 and generates a controlled axial expansion of the axial support 16 or axial movement of either the proximal support member 14 or the distal support member 12 relative to the axial support 16. The force measuring mechanism 22 is affixed to the axial support 16 or between the axial support 16 and either the distal support 12 or the proximal support 14. The force measuring mechanism 22 may be permanently affixed to the structure or it may be removably affixed to the traction splint 10 so that it can be removed once the amount of traction force has been determined.

Referring to FIG. 1A, the axial support locks 18 are spring-loaded pins, preferably with a hemispherical end, affixed to the inner telescoping member or members of the axial support 16. They project outward through holes the outer telescoping member or members of the axial support 16. To telescope the axial support 16, one depresses the spring-loaded pin to a position inside that of the outer telescoping member of the axial support 16. The axial support inner and outer members are then moved axially to the desired location. The spring-loaded pin advances under its own force outward through another hole in the outer support member. FIG. 1A depicts three such spring-loaded pins and a plurality of holes in the axial support 16 through which the pins can be aligned. This configuration generates a plurality of discreet lengths at which the axial support 16 may be telescoped and locked. Any other form of locking means, such as cam clamps, toggle clamps, or other suitable telescopic locking means.

Referring to FIG. 1A, the distal support structure 12 is configured to apply tension to the damaged limb by application of compression force to the top of the foot. The distal support structure 12 is configured as a cuirass that opens and surrounds the lower leg just above the foot. The distal support structure 12 is closeable after surrounding the lower leg and locks in place using apparatus such as, but not limited to, a clamp, clip, buttons, snap, belt and buckle, Velcro® or other hook and loop fabric fastener, and the like. The distal support structure 12 secures the foot longitudinally relative to the telescoping splint, and applies compression force to the top of the foot, thus generating a traction force on the leg. The distal support structure 12 evenly distributes the applied traction force for maximum comfort and minimum trauma to the foot. The distal support structure 12 is affixed to the lower or distal end of the axial support 16 so that it does not distort or undergo torsion and remains in a plane generally perpendicular to the axis of the axial support 16.

Referring to FIG. 1A, the proximal support structure 14 is configured to be closeable after surrounding the leg and locks in place using apparatus such as, but not limited to, a clamp, clip, buttons, snap, belt and buckle, Velcro® or other hook and loop fabric fastener, and the like. The proximal support structure 14 fixes the proximal end of the telescoping splint to a proximal region of the leg (the upper calf or thigh, depending on the location of the fracture) and generates compression force toward the body and, in concert with the distal support structure 12, generates traction on the leg. The proximal support structure is configured so as not to undergo torsion or distortion out of its primary plane, which is generally orthogonal to the axis of the axial support 16.

Referring to FIG. 1A, the axial support 16 is fabricated preferably from Radiolucent materials so that X-rays or fluoroscopic images may be taken of the limb without undue obscuration of the image by radiopaque denseness of the material. The axial support 16 and all other components of the traction splint 10 are preferably fabricated from materials that are non-magnetic and thus do not generate image distortion, heat, or motive force while being imaged by magnetic resonance imaging (MRI). Preferred materials for fabrication of the axial support and structural members of the proximal support structure 14 and distal support structure 12 include, but are not limited to, carbon fiber, fiber composites, polyurethane, polyethylene, polyvinyl chloride, polypropylene, fiberglass, polycarbonate, polyimide, glass-filled polymers, and the like. The wall thickness shall be thin enough that radiodensity is minimized and radiograph clarity is maximized. The axial support 16 and other structural members of the traction splint 10 shall comprise sufficient integrity to generate and maintain between 1 and 100 pounds of traction force on the limb, preferably between 5 and 50 pounds of traction force, and most preferably between 7 and 30 pounds of force, without failure or distortion.

Referring to FIG. 1A, the traction force generating mechanism 20 is capable of extending the length of the axial support 16 or moving the proximal support 14 or the distal support 12 relative to the axial support in a controlled manner. Backlash and recoil preferably do not occur. A lever to provide mechanical advantage to make the application of force easy for the caregiver is comprised by the traction force generating mechanism 20. The traction force generating mechanism 20 comprises apparatus such as, but not limited to, a jack-screw, a cam, an adjustable or non-adjustable spring, an adjustable or non-adjustable magnetic attractor, a pneumatic or hydraulic cylinder, a pneumatic bellows, and the like. In one embodiment, the traction force generating mechanism 20 comprises a coarse adjustment and a fine adjustment. The coarse adjustment may be accomplished by apparatus such as telescoping bars with pins and holes, a cam, a gear, or other device known to persons skilled in the art of applying force. A fine adjustment is accomplished using gears with finer tooth spacing or other devices with mechanical advantage whose control surfaces move considerably further than the structural elements that exert the traction force. Once the traction force has been applied, it is maintained by the traction force generating mechanism 20 until the caregiver releases the force. A lock or other device is preferably comprised by the traction force generating mechanism 20 to ensure that the traction force is maintained until relief is desired.

Referring to FIG. 1A, the traction force measuring mechanism 22 is a device such as, but not limited to, a force gauge, a strain gauge, a pressure gauge, an optical interferometer, or the like. The traction force measuring mechanism 22 comprises a display such as, but not limited to, a digital readout, a CRT, a flat panel display, an LCD, optical indicator such as a series of LEDs, and the like. The traction force measuring mechanism 22 optionally comprises an audio output device. The audio output device or the visual display are configured to notify the operator of the traction force being generated as well as other system parameters such as battery power, system status, and the like. Any visual displays are preferably configured to be read in low-light environments and when conditions are inclement such as in the rain, snow, etc.

Figure 1B:
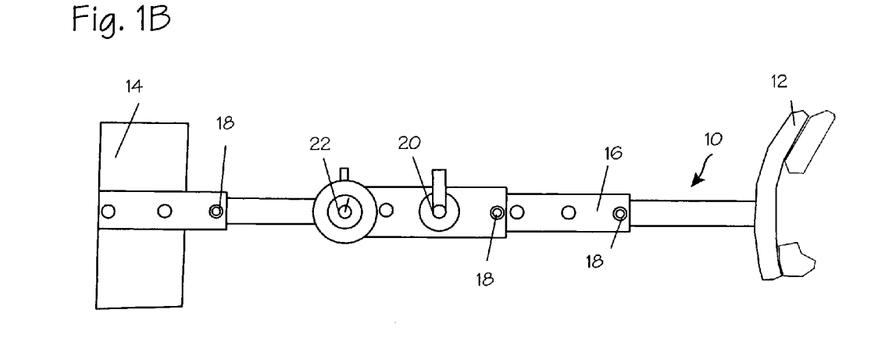

FIG. 1B illustrates a traction splint 10 in its fully expanded configuration. The axial support 16 further comprises telescoping members that slide axially with respect to each other without becoming misaligned. The axial support 16 locks at discreet locations using the plurality of axial support locks 18. Continuously variable extension of the axial support 16 extension with locking capability may be accomplished with set-screws, cam clamps, toggle clamps and other suitable telescopic locking means.

Figure 1C:
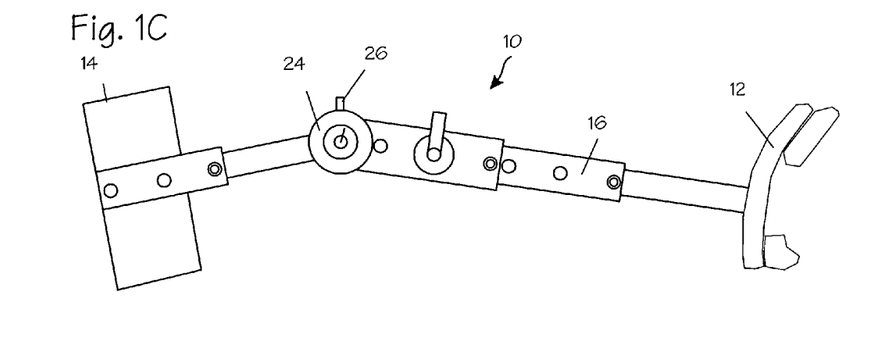

FIG. 1C illustrates a traction splint 10 in its fully expanded configuration but articulated at a point along the axial support 16. The articulation joint 24 is affixed to the axial support 16 at a point intermediate to its proximal and distal end. The articulation joint 24 provides a pivot point to rotate, bend, or articulate the axial support 16 to provide maximum support benefit to the limb. The articulation joint 24 further comprises an articulation lock 26 that may be selectively and controllably locked and unlocked to maintain the desired amount of articulation or bending.

Figure 2A:
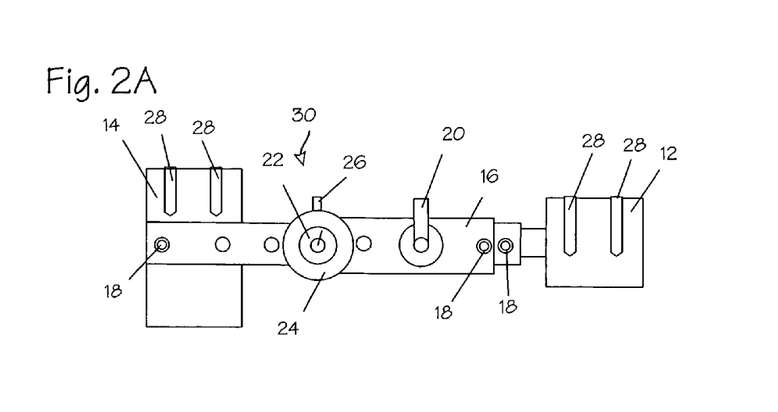
FIGS. 2A and 2B illustrate an arm traction splint.

FIG. 2A illustrates a traction splint 30 configured for use on an arm, in its compressed or retracted configuration. The arm traction splint 30 further comprises a distal support member 12, a proximal support member 14, an axial support 16, a plurality of axial support locks 18, a traction generating mechanism 20, a traction measuring mechanism 22, an articulation joint 24 and an articulation lock 26. The proximal support member 14 and the distal support member 12 further comprise a plurality of locking straps 28. The arm traction splint 30 is similar to the leg traction splint 10 except that the arm traction splint 30 is shorter overall and the proximal support member 14 and the distal support member 12 are adapted to secure the splint to the arm. The distal support member 12 is configured to surround the patient at or above the wrist to generate the traction force on the arm, and to impede movement of the hand proximally relative to the support member. The articulating joint 24 is configured to reside at or near the elbow. An intermediate support may be added to stabilize the arm in the central region of the arm traction splint 30. The plurality of axial support locks 18 are engaged into locking holes in the axial support 16 to maintain the compressed configuration.

Figure 2B:
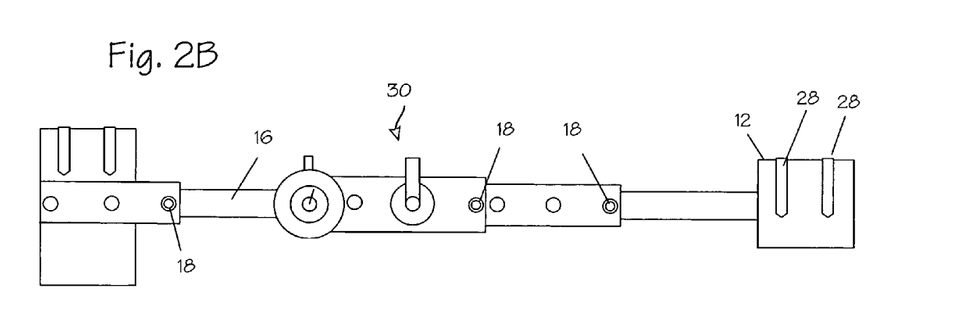

FIG. 2B illustrates the arm traction splint 30 in its fully expanded configuration. Referring to FIGS. 2A and 2B, the plurality of axial support locks 18 are engaged into locking holes in the axial support 16 to maintain the expanded configuration.

Figure 3A:
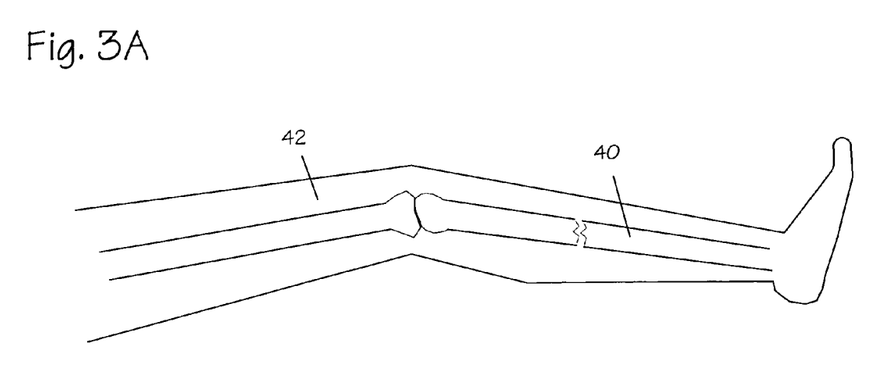
FIGS. 3A and 3B illustrate a side view of a leg with a fracture to the tibia or bone of the lower leg and its treatment with the leg traction splint.

FIG. 3A illustrates a fracture to a tibia 40, a bone in the lower part of a leg 42.

Figure 3B:
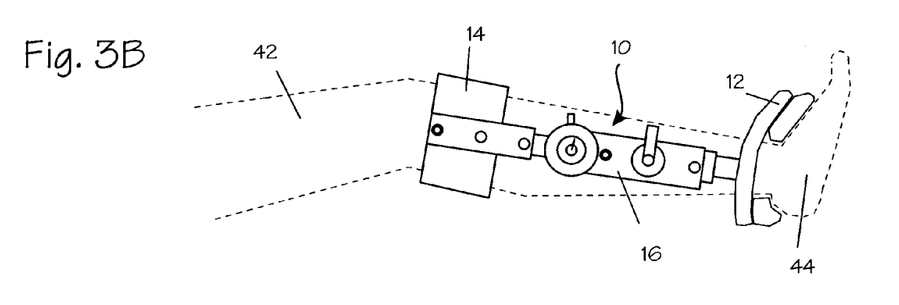

FIG. 3B illustrates the fracture to the tibia (not shown) in the lower part of the leg 42 with a leg traction splint 10 applied. Referring to FIGS. 1A, 3A, and 3B, the distal support member 12 engages the top of the foot 44 and generates a caudal or downward force on the foot 44, as well as a distal force on the foot. The proximal support member 14 is engaged with the leg 42 just below the knee, although in another embodiment, it is engaged above the knee. The proximal support member 14 generates superiorly directed or upward force on the leg 42 by friction force, enhanced by compressive force on the leg and the generally outward taper of the leg 42 moving from the foot 44 to the pelvis. The fractured tibia 40 (not shown) is relieved of compressive stresses by the traction splint 10. The axial support 16 is slightly, but not fully, expanded in this configuration.

Figure 4A:
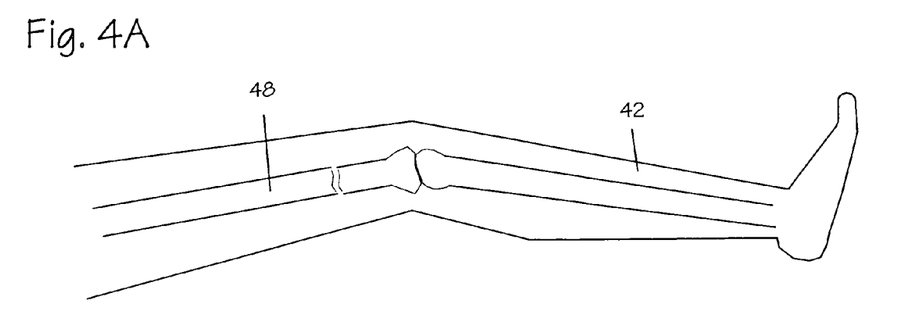
FIGS. 4A and 4B illustrate a fracture of the lower femur and use of the leg traction splint with its limb contacting regions adjusted to treat a fracture of the lower femur.

FIG. 4A illustrates a fracture to the lower part of a femur 48, a bone in the upper part of a leg 42.

Figure 4B:
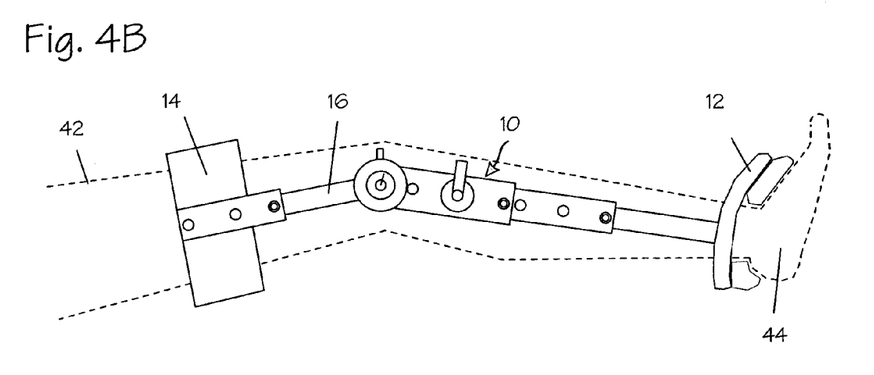

FIG. 4B illustrates the fracture to the femur (not shown) in the upper part of the leg 42 with a leg traction splint 10 applied. Referring to FIGS. 1A, 4A, and 4B, the distal support member 12 engages the top of the foot 44 and generates a caudal or downward force on the foot 44. The proximal support member 14 is engaged with the upper part of the leg 42 in the middle of the thigh, but may be engaged at the thigh just below the pelvis, or at the ischium of the pelvis. The proximal support member 14 generates superiorly directed or upward force on the leg 42 by friction force, enhanced by compressive force on the leg and the generally outward taper of the leg 42 moving from the foot 44 to the pelvis. The fractured femur (not shown) is relieved of compressive stresses by the traction splint 10. The axial support 16 is nearly, but not completely, expanded in this configuration.

Figure 5A:
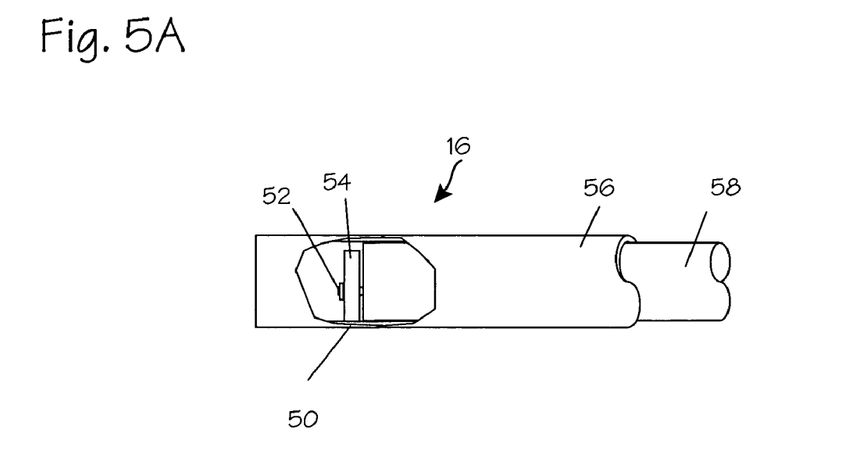
FIGS. 5A and 5B illustrate traction splint expansion locking mechanisms.

FIG. 5A illustrates one embodiment of a locking mechanism 50 for the telescoping axial support 16. The locking mechanism 50 is an offset cam that comprises an axle 52, an offset cam lock 54, an exterior tube 56, and an interior tube 58. The exterior tube 56 and the interior tube 58 are axially elongate. They are preferably round in cross-section and have an interior and an exterior surface but they may also be slightly elliptical or oval in cross-section. They may even be square or rectangular in cross-section in areas not near the offset cam lock 50. They slideably move axially relative to each other and also move rotationally relative to each other. The axle 52 is affixed to the end of the interior tube 58. The offset cam lock 54 is a circular, elliptical, or oval component that frictionally engages the interior of the exterior tube 56. The axle 52 projects through a hole in the offset cam lock 54, the hole being located off center of the offset cam lock 54. By manually or remotely telescoping or axially moving the exterior tube relative to the interior tube 58, the desired length is selected. By manually or remotely rotating the interior tube 58 relative to the exterior tube 56, the offset cam lock 54 is compressed against the interior of the exterior tube 56 with increasing force and friction to prevent further axial motion. Counter rotating the two tubes in the other direction will relieve the friction and eliminate the lock between the interior tube 58 and the exterior tube 56.

Figure 5B:
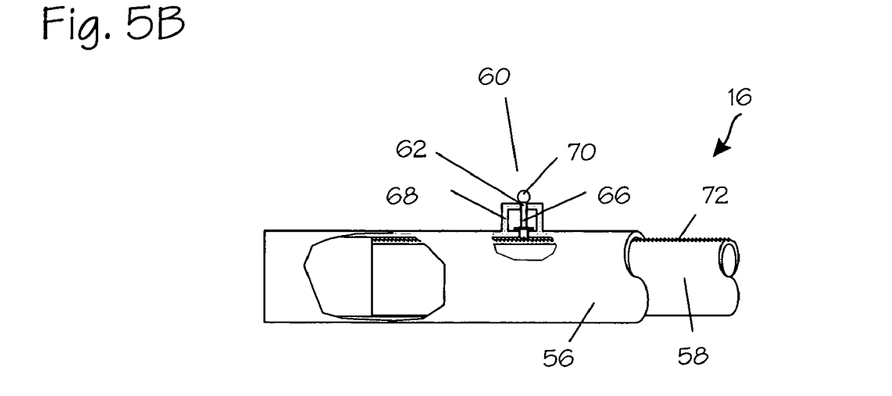

FIG. 5B illustrates one embodiment of a locking mechanism 60 for the telescoping axial support 16. The locking mechanism 60 is a spring loaded pin lock that comprises a pin 62, a linear line of teeth 72, a spring 66, a lock housing 68, a knob 70, an exterior tube 56, and an interior tube 58. The interior tube 58 is axially elongate and slides axially with respect to the exterior tube 56, which is also axially elongate. The interior tube 58 and the exterior tube 56 are generally hollow with an interior wall and an exterior wall but they need not be complete tubes, nor need they be round in cross-section. The lock housing 68 is affixed to the exterior tube 56 and supports the pin 62 and the spring 66. The knob 70 is permanently affixed to the outermost part of the pin 62. The spring 66 is trapped by the pin 62 and the lock housing 68 so as to generate an inwardly biased compressive force on the pin 62. The pin 62 engages with teeth 72 on the interior tube 58 to engage the lock. To disengage the lock, the pin 62 is withdrawn manually, by the knob 70, against the spring 66 and away from the teeth 72 on the interior tube 58. The interior tube 58 and the exterior tube 56 are now slidably movable relative to each other and may be relocked at a different location. Preferably the interior tube 58 is not rotationally movable relative to the exterior tube 56. Preferably, the pin 62 has multiple edges on its innermost end to facilitate entry into the teeth 72. In another embodiment, a ratchet mechanism is provided to allow the interior tube 58 to slide in one direction only relative to the exterior tube 56 without withdrawing the pin 62. To move in the other direction, the direction of the compressive force generated by a traction mechanism, the pin 62 must be withdrawn. In yet another embodiment the line of teeth 72 on the interior tube 58 is replaced by a plurality of holes through which the pin 62 selectively projects when aligned with the holes.

The upper and lower traction elements, in a further embodiment, are integral to the backboard and fold into the backboard when not in use. The traction elements are unfolded out of the backboard when needed.

In yet another embodiment, the backboard with the integral traction splint, further comprises a section that selectively folds out to elevate one or both legs. The leg elevation region comprises optional padding. The leg elevation region further comprises an optional articulation region that permits the knee to bend. The amount of leg elevation and leg articulation may be variable and controllable or they may be preset to certain preferred levels. A similar feature optionally is provided for arm elevation and articulation if required.

In a further embodiment, the traction splint is provided integral to the backboard. The traction elements slide up and down along the backboard in a groove or slot. The traction elements have the capability of locking into the groove or slot in the backboard. When the patient is to be removed from the backboard, the upper traction element, a longitudinal element, and the lower traction element are separated from the backboard and stay with the patient. The upper and lower traction elements and the longitudinal support are disposable. A new disposable upper traction element, lower traction element and longitudinal support are reloaded onto the backboard or stretcher for the next case. This disposability allows for the traction splint to stay with the patient throughout their early therapy and for the stretcher or backboard to be immediately reused on another patient with a new disposable traction apparatus.

In yet a further embodiment of the traction splint with the integral backboard, the traction elements are disposed within releasable slots in the backboard. The traction elements are removable from the backboard so as to stay with the patient. The removable traction splint traction elements further comprise a removable longitudinal support that is normally integral to the backboard or a separately added piece. The separately added longitudinal support is attached to the traction elements once the correct amount of traction and appendage orientation have been determined. The longitudinal support is added through lockable elements in the traction elements to maintain their orientation and traction following removal from the backboard. Alternatively, the longitudinal support is that region of the backboard that holds the traction elements. This region is capable of being unlocked, detached, or removed from the backboard so as to stay with the traction elements.

In yet another embodiment of the invention, an adult and a pediatric backboard traction splint combination is provided due to the extreme differences in sizes of these types of patients.

Using the methods of the present invention, a patient is placed directly upon the backboard. The lower traction element is folded out and placed in contact with the top of the foot and locked in place so as to be able to provide axial caudal traction force on the foot. The lower traction element is advanced axially caudally until the desired traction force is applied to the foot. The leg is optionally elevated prior to applying the traction.

Figure 6A:
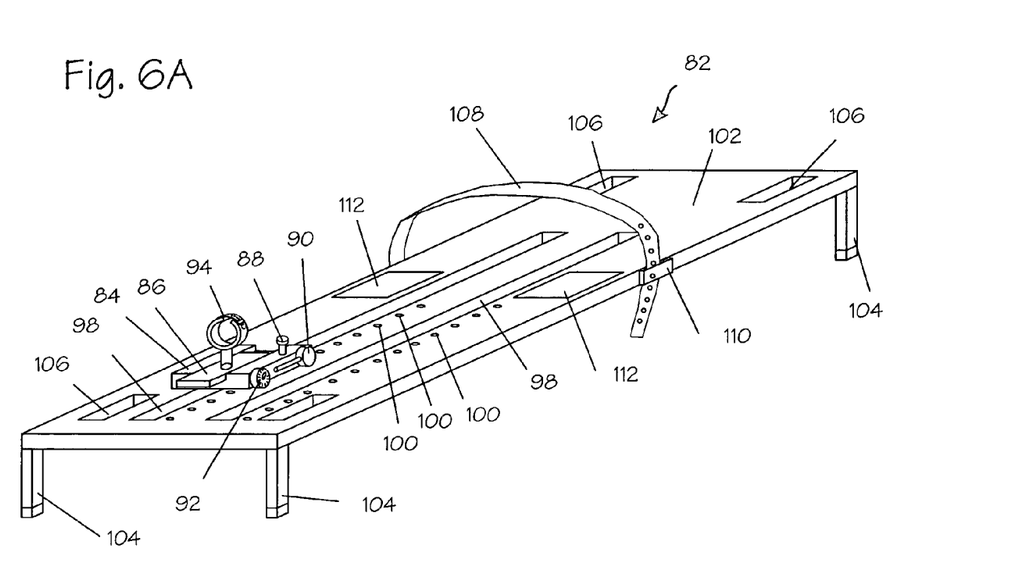
FIGS. 6A and 6B illustrate an oblique view of a leg traction splint integrated with a backboard.
Figure 6B:
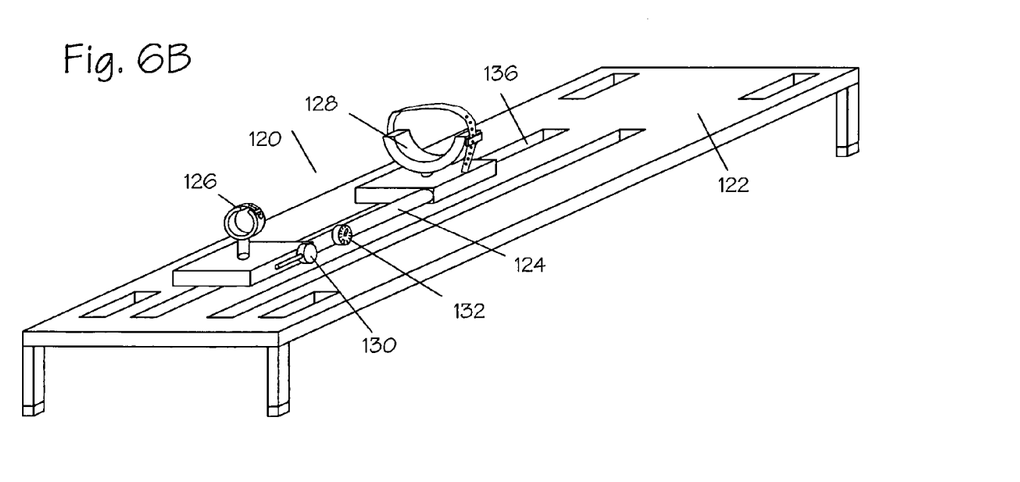

FIGS. 6A and 6B illustrate the apparatus adapted for generating traction on a limb having a bone fracture by securing the patient to a a backboard adapted to accommodate a patient and support a patient under a substantial portion of the patient's body and a substantial portion of the roken limb. A distal limb support member adapted to secure the limb at a point distal to the bone fracture is distally movable relative to the backboard. Means for fixing the distal support member in relation to the backboard and the limb are provided. and proximal support means for securing the patient to the backboard at a point superior to the bone fracture (either the thigh or proximal point on the limb, or the patients torso) are use to fix the proximal portion of the broken limb. The telescoping splint may be fixed to a backboard, as shown in FIG. 6B, or the axial adjustment of the distal and proximal support means may be provided by making one or both slidably upon the backboard, as shown in FIG. 6A.

FIG. 6A illustrates a traction splint 80 integrated with a backboard 82. The traction splint 80 further comprises a lock down plate 84, a traversing stage 86, a lock down pin 88, a traction generating mechanism 90, a traction measuring mechanism 92, and a distal support structure 94. The backboard 82 further comprises one or more longitudinal T-slots 98, a plurality of locking holes or detents 100, a main board 102, a plurality of legs 104, a plurality of carrying handles 106, a chest strap 108, and a chest strap lock 110.

Referring to FIG. 6A, the traction splint 80 is slidably affixed to the main board 102 of the backboard 82 through the longitudinal T-slot 98. A projection, affixed to the bottom of the lock down plate 84 passes through the longitudinal T-slot 98 and is terminated with a "T" or other wide profile to retain the lock down plate 84 in close proximity to the main board 102. The lock down pin 88 serves to hold the position of the lock down plate at a desired location by engaging with the holes or detents 100 in the main board 102. The traversing stage 86 is slidably affixed to the lock down plate 84. The traversing stage 86 is permanently affixed to the distal support structure 94. The traction generating mechanism 90 is affixed to the lock down plate 84 and moves the traversing stage 86. The traction generating mechanism 90 comprises a handle, lever, knob, motor, or other manual or remote adjustment mechanism and further comprises gearing or other mechanical advantage to controllably, forcibly, and easily move the traversing stage 86 relative to the lock down plate 84. In another embodiment, the traction generating mechanism 90 is a spring with permanent or adjustable force, or a magnetic attraction system powered by electromagnets or permanent magnets such as those fabricated from neodymium iron cobalt. The height of the distal support 94 is preferably adjustable and reversibly lockable at a desired distance from the main board 102. The height of the distal support 94 is preferably capable of being adjusted above or below the upper surface of the main board 102. Below the main board 102 height settings require an opening in the main board to accommodate the foot, leg, and distal support 94. The traction measuring mechanism 92 is a force or pressure readout similar to that described for the leg traction splint in FIGS. 1A, 1B, and 1C. The distal support structure 94 comprises components that are the same as those described in the distal support structure 12 disclosed in FIGS. 1A, 1B, and 1C.

Referring to FIG. 6A, the plurality of legs 104 on the backboard preferably may be folded up against the main board 102 for space-saving in storage. The plurality of legs 104 may be opened to their perpendicular positions and locked in place. The plurality of legs 104 further preferably comprise telescoping or folding extensions to permit height adjustment and securing or locking at the desired height. The plurality of carrying handles 106 are preferably slots or cutouts in the main board 102, or they may be straps, handles with standoffs, and the like. The chest strap 108 passes around the chest, preferably under the arms and secures the patient's torso to the backboard main board 102. The chest strap 108 is permanently affixed to one side of the main board 102 and reversibly affixed to the other side of the main board 102 using the chest strap lock 110. The chest strap lock may comprise mechanisms such as, but not limited to, Velcro® or other hook and loop fabric fastener, buttons, snaps, buckles and pins to engage holes in the chest strap 108, and the like. The chest strap 108 is fabricated from materials such as, but not limited to, woven materials, solid materials, nylon, polyester, and the like, all, preferably flexible but inelastic. The chest strap 108 serves the function of the proximal support structure 14 in FIG. 1A. It secures the upper part of the patient from moving caudally, while caudal force is being generated by the distal support structure 12. The chest strap 108 may be replaced by, or augmented by bumps, or projections from the main board 102 that are, preferably padded, and fit under the arms of the patient in the region of the armpit. Such projections or bumps also serve to keep the patient from moving caudally under caudal force. The projections or bumps are long enough to firmly engage the patient's underarms and preferably project upward at least half the thickness of the arm and preferably the full thickness of the body at the shoulder.

Referring to FIG. 6A, in another embodiment of the invention, the locking pin 88 has at least one tooth and preferably a plurality of teeth that engage with teeth in the main board. The locking pin 88 may also comprise a cam lock to frictionally engage the main board through a slot rather than holes 100.

Referring to FIG. 6A, the main board 102 and the legs 104 are preferably fabricated from radiotransparent or radiolucent and non-magnetic materials such as, but not limited to, polyurethane, polyethylene, polypropylene, polystyrene, polyvinyl chloride, acrylics, polyimides, carbon composites, cardboard, corrugated cardboard, fiberboard, wood, foamed materials, glass or other material reinforced polymers, and the like.

Referring to FIG. 6A, the main board 102, in another embodiment, further comprises a standoff or rest that is placed under the knee of the patient to raise the leg, support the knee from below, and maintain a prescribed amount of bend in the knee whether the leg is under traction or not. The standoff projects upward from the main board 102 and is adjustable or positionable under one or both legs at various positions. The standoff is further capable of being secured or locked to the main board 102.

Referring to FIG. 6A, in yet another embodiment, the main board 102 further comprises a pad 112 of foam or elastomeric material that is positioned under the hip. The surface of the foam or elastomeric material further comprises ripples, dimples, or other structures that enhance friction with the patient. The weight of the patient causes the pad 112 of foam or elastomeric material to deform and frictionally support the pelvis so that it does not slide or translate relative to the main board 102 when the leg is placed under traction. The foam or elastomeric pad 112 is fabricated from standard low durometer materials such as, but not limited to, C-flex, polyurethane foam, polyvinylchloride foam, and the like. The foam is preferably closed-cell but could be open cell and is further preferably enhanced by a surface coating of mildly adhesive materials to increase the surface friction against the patient. The pad 112 deforms and conforms to the contours of the body to assist in generating friction between the patient and the backboard 82.

Referring to FIG. 6A, the backboard 82 may further comprise wheels and a yoke so that one person can attach themselves to the backboard and pull the backboard along on the wheels, preferably with their hands free. The backboard 82 may further comprise skids or runners suitable for use in snow or ice. The backboard 82 may further comprise inflatable compartments or hollow internal structure that provides buoyancy or flotation to the backboard 82 and a person carried thereon. The backboard 82 may be foldable laterally and or longitudinally. The backboard 82 may be collapsible and inflatable using air.

The wheels may be spherical and roll in sockets rather than disc-shaped and on axles. The backboard 82 may comprise a covering to secure the patient thereon. The covering may comprise materials such as Kevlar that are resistant to penetration and thus protect the patient from external dangers. The hollow wheels, disc-shaped or spherically shaped, may serve as flotation devices for the backboard 82. The backboard 82, of this embodiment, is especially well suited to military applications so that a single soldier can remove an injured soldier to safety without the need for additional help in carrying the stretcher. The single soldier can further carry and use a weapon while transporting the injured soldier since the transporting soldier has their hands free during transport.

FIG. 6B illustrates a traction splint 120 removably affixed to a compatible backboard or stretcher 122. The traction splint 120 further comprises an axial support 124, a distal support 126, a proximal support 128, a traction generating mechanism 130, a traction measuring mechanism 132, a backboard attachment mechanism 134 (not shown), and an attachment slot 136.

Referring to FIG. 6B, the traction generating mechanism 130 is the same as that described in FIG. 1A or, in another embodiment, the same as that described in FIG. 6A. The distal support 126 is the same as that described for FIG. 1A or 6A. The backboard attachment mechanism 134 is, for example, a spring-loaded T-clamp that is inserted through holes in the proximal support 128 and the distal support 126. The backboard attachment mechanism 134 projects through the attachment slot 136 and is rotated so that a wide flange or "T" structure interferes with the slot and prevents the proximal and distal supports from being withdrawn away from the backboard 122. The backboard attachment mechanism 134 preferably comprises a handle that allows for manipulation of the attachment mechanism 134 to lock and unlock the traction splint 120 from the backboard 122. In other embodiments, the backboard attachment mechanism 134 comprises a Velcro® or other hook and loop fabric fastener system, a snap, a buckle, a button, a strap, a magnetic latch, or the like. The proximal support mechanism 128 comprises, in a preferred embodiment, a friction pad affixed to the backboard or stretcher and a strap or other structure that forces or coerces the torso, which further comprises the thorax, abdomen, or pelvis, against the friction pad. The proximal support mechanism 128 of this embodiment gently supports the patient and allows the distal support 126 to provide the desired traction to provide the required stabilization function.

Referring to FIG. 6B, the traction measuring mechanism 132 is optional as is the case on all the traction splints. The traction measuring mechanism 132 is preferably optional if the level of traction is pre-set such as with a spring or a pre-calibrated adjustment.

In use, a patient is placed directly upon the backboard. The lower, or distal, traction element is folded out and placed in contact with the top of the foot and locked in place so as to be able to provide axial caudal traction force on the foot. The lower traction element is advanced axially caudally until the desired traction force is applied to the foot. The leg is optionally elevated prior to applying the traction.

Figure 7A:
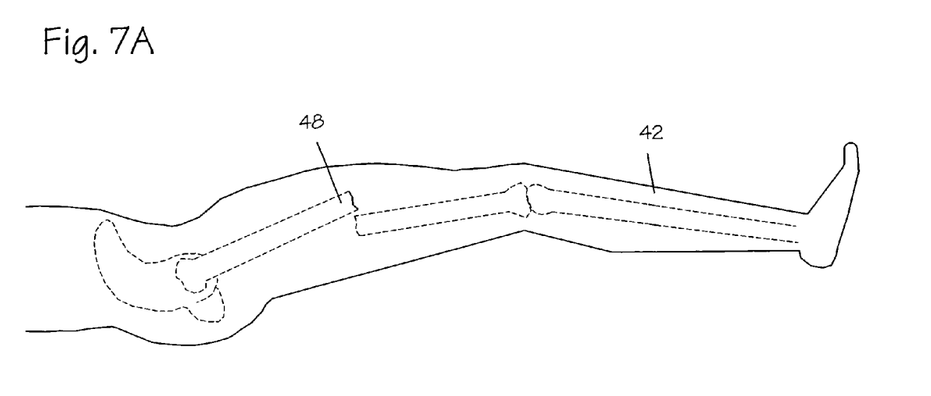
FIGS. 7A and 7B illustrate a fracture to the upper femur and treatment with a leg traction splint comprising an ischial saddle and a foot saddle.

FIG. 7A illustrates a fracture to the middle or upper part of a femur 48, a bone in the upper part of a leg 42.

Figure 7B:
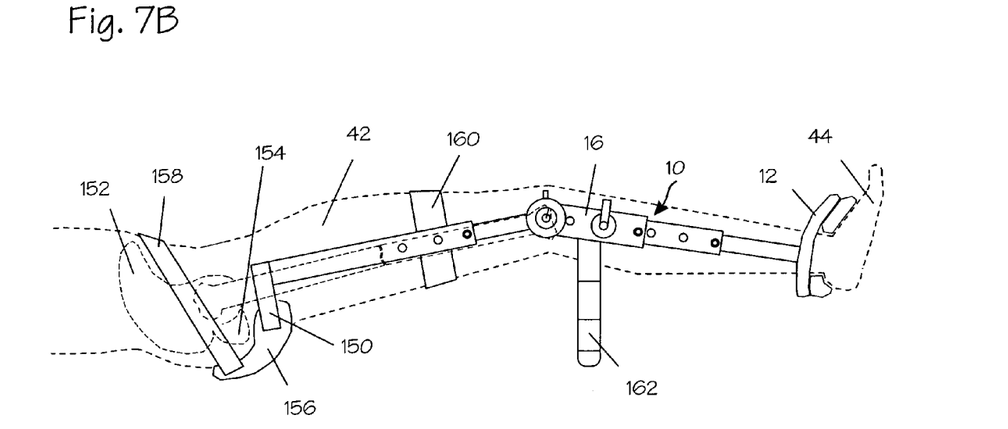

FIG. 7B illustrates the fracture to the femur (not shown) in the upper part of the leg 42 with a leg traction splint 10 applied. Referring to FIGS. 1A, 4A, and 4B, the distal support member 12 engages the top of the foot 44 and generates a caudal or downward force on the foot 44. The proximal support member 150 is engaged with the pelvis 152 at the ischium 154. The proximal support member 150 generates superiorly directed or upward force on the leg 42 by direct compression on the ischium 154. The fractured femur 48 (not shown) is relieved of compressive stresses by the traction splint 10. The axial support 16 is completely, expanded in this configuration. The proximal support 150 is engaged with the ischium 154 by a padded bar 156 and a strap 158 to secure the padded bar 156 against the ischium 154. The strap 158 is secured by standard fasteners including those comprising buckles, snaps, buttons, Velcro® or other hook and loop fabric fastener, and the like. The leg traction splint 10 further comprises a central support 160 and a standoff 162. The central support 160 is a padded or unpadded strap, preferably padded, that stabilizes the leg 42 at the central region of the leg traction splint 10 and maintains close proximity between the leg 42 and the leg traction splint 10. The standoff 162 preferably folds up parallel to the axial support 16 and locks in place when not in use. The standoff 162 is selectively adjustable at an angle to the axial support 16 and locks in place at the desired orientation. The standoff 162 further preferably comprises telescoping or adjustable height that is lockable at a desired length.

Figure 8A:
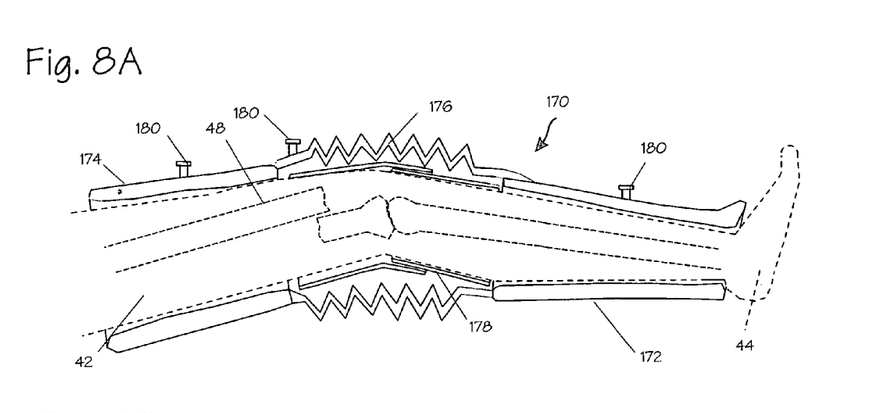
FIGS. 8A, 8B and 8C illustrate a deflated traction splint comprising an inflatable structure applied to a leg.

FIG. 8A illustrates another embodiment of the leg traction splint 170 utilizing inflatable components. The leg traction splint 170 comprises a distal support 172, a proximal support 174, a traction bellows 176, and a protective sleeve 178. The distal support 172, the proximal support 174, and the traction bellows 176 all further comprise inflation ports and valves 180. FIG. 8A further depicts the traction splint 170 being applied to treat a leg 42, with a foot 44, comprising a fracture to the lower part of the femur 48. The traction splint 170 has been applied to the leg 42 but not inflated in FIG. 8A.

Referring to FIG. 8A, the distal support 172 surrounds the leg 42 just above the foot 44. The proximal support 174 surrounds the upper leg and is preferably engaged against the pelvic region at its proximal-most end. Both the distal support 172 and the proximal support 174 are preferably C-Shaped inflatable structures that are wrapped around the leg 42 and secured in place with straps, fasteners, Velcro® or other hook and loop fabric fastener, or the like. The C-shaped inflatable structures generally comprise an outer wall and an inner wall, sealed together or integral to each other and an inflatable chamber or space therebetween. An inflation port and valve 180 allows for pressurized gas or liquid to be inserted or injected into the chamber or space. Once the fluid (gas or liquid) has been placed into the chamber or space, the valve prevents escape. The valve 180 is an openable valve such as a stopcock or it preferably is a one-way valve that permits inflation with automatic prevention of fluid escape. A manual override to deflate the chamber is preferred.

Figure 8B:
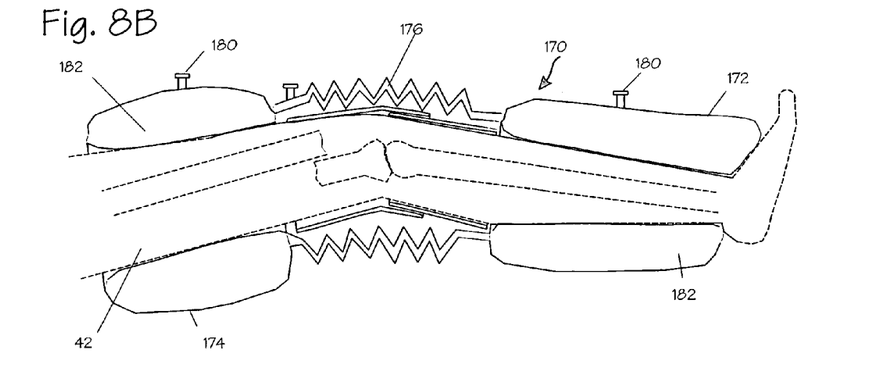

FIG. 8B illustrates the leg traction splint 170 with the proximal support 174 and the distal support 172 inflated and the plurality of chambers 182 are also shown. By inflating the chamber 182 the inner wall is forced against the leg 42, which causes that section of the leg 42 to be stabilized. The inner wall further causes frictional forces to exist that prevent relative motion of the proximal support 174 and distal support 172 relative to the leg 42 once traction force has been generated. The leg traction splint 170 preferably also comprises a standoff (not shown), inflatable or non-inflatable, to position the leg 42 relative to a gurney, backboard, bed or stretcher. The traction bellows 176 has not yet been inflated and traction has not yet been applied to the leg 42.

Figure 8C:
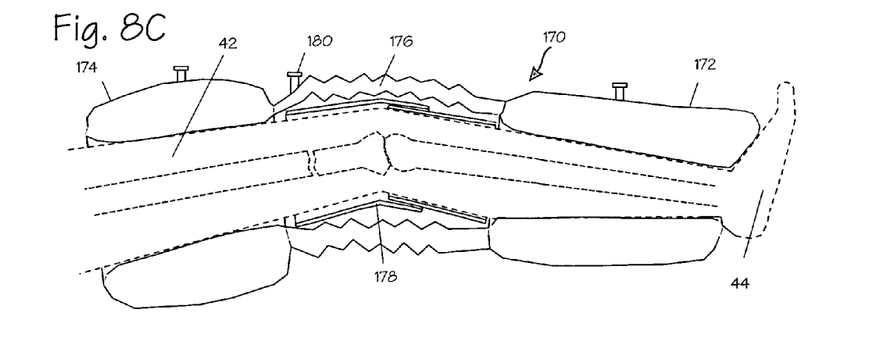

FIG. 8C illustrates the leg traction splint 170 with its proximal support 174, the distal support 172, and the traction bellows 176 inflated or pressurized. The protective sleeve 178 surrounds the leg and resides between the leg 42 and the traction bellows 176. The protective sleeve 178 provides outwardly directed resistance against any inward forces that might be created by the inflatable traction bellows 176. The protective sleeve 178 in a preferred embodiment comprises two or more segments that telescope against each other to permit longitudinal motion of the leg 42 inside the traction splint 170. The protective sleeve 178 is loosely applied to the leg 42 and does not provide any inward force against the leg 42. The protective sleeve 178 is axially elongate and is preferably open on one side by way of a slit or slot so it can be placed on the leg 42, or it is slid onto the leg 42 over the foot 44 and therefore not need to be slotted axially.

Referring to FIG. 8C, the traction bellows 176 are disposed between the proximal support 174 and the distal support 172 and exerts a separation force on the two supports. The separation or traction force is generated by inflating the traction bellows 176. Inflation of the traction bellows 176 to a specified pressure generates a specific axial force separating the proximal support 174 and the distal support 172. The traction bellows 176 has restricted outward and inward expansion and its primary expansion is in the axial direction only. The restriction on outward and inward expansion of the traction bellows 176 is created by stiffening members and inelastic materials. Inflation of the traction bellows 176 causes corrugations or undulations in the bellows to straighten out generating a length increase under a force. Inflation is generated through a port and valve 180. Inflation pressure is preferably monitored using a pressure gauge that is integral to or removable from the inflation port 180. The traction bellows 176 may, in another embodiment, comprise mechanisms such as, but not limited to, hydraulic cylinders, pneumatic cylinders, jack screws, cam levers, and the like. Pneumatic inflation or hydraulic inflation is accomplished using any suitable pump.

The splint system may be embodied in other specific forms without departing from its spirit or essential characteristics. For example, the proximal and distal supports may be cuirass-type devices, pads with straps and belts, or inflatable collars. The traction generating mechanism can be a jack-screw, an inflatable bellows, or a pulley system, among other options. The mechanical and pneumatic traction splints may be hybrid and use some of the components of the other type of traction splint. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

What is claimed is:

1. A method of generating traction on a damaged limb of a patient that involves the steps of:

releasably affixing a traction-generating device to a backboard, said traction generating device comprising a proximal support member, a distal support member, and an axial support member; wherein the distal support member is substantially at the distal end of the traction-generating device;

placing a patient on the backboard;

adjusting a telescoping section of the traction-generating device to fit the patient;

locking the telescoping section of the traction-generating device at a desired length;

affixing a proximal support member to a limb region closer to the body relative to the damaged region of said limb;

affixing a distal support member to a limb region further from the body relative to the damaged region of said limb;

applying tension on said damaged limb by generating compressive forces within said telescoping section of said traction generating device; and imaging the damaged limb while said traction generating device is still operably attached to the damaged limb of said patient.

2. The method of claim 1 wherein said imaging comprises acquisition of X-ray or fluoroscopic images or analysis.

3. The method of claim 1 further comprising the step of measuring the amount of said compressive forces in said axial support member.

4. The method of claim 1 further comprising the step of removing the traction generating device and patient from the backboard while maintaining traction on the damaged limb.

5. An apparatus adapted for generating traction on a limb having a bone fracture, said apparatus comprising:
- a backboard adapted to accommodate a patient and support a patient under a substantial portion of the patient's body and a substantial portion of the patient's limb;
- a distal limb support member, said distal limb support member adapted to secure the limb at a point distal to the bone fracture, said distal support member being distally movable relative to the backboard;
- means for fixing the distal support member in relation to the backboard and the limb;
- a proximal support means for securing the patient to the traction generating apparatus at a point superior to the bone fracture; and
- an axial support member for fixing the distal support member in relation to the proximal support means and generating compressive forces to move the distal support member away from the proximal support means;
- wherein the proximal support means, the distal support member, and the axial support form a traction generating device that is releasably attached to the backboard such that the relationship between the proximal support means and the distal support means is fixed; and
- wherein the distal support member is located substantially at the distal end of the traction-generating device.

6. The apparatus of claim 5 wherein the distal support member is adapted to secure the patient's foot in fixed relation to the backboard, and the proximal support means is adapted to secure the patient's chest or abdomen to the backboard.

7. The apparatus of claim 5 wherein the distal support member is adapted to secure the patient's foot in fixed relation to the backboard, and the proximal support means is adapted to secure the patient's thigh to the backboard.

8. The apparatus of claim 5 wherein all components are fabricated from non-magnetic materials.

9. The apparatus of claim 5 wherein all components are fabricated from radiolucent materials.

10. The apparatus of claim 5 wherein the means for fixing the distal support member in relation to the backboard and the limb comprises a telescoping splint and means for fixing the telescoping splint to the backboard.

11. The apparatus of claim 5 wherein the axial support member comprises a telescoping splint and means for releasably attaching the telescoping splint to the backboard.

12. The apparatus of claim 11 wherein the telescoping splint further comprises a controllable, lockable, articulating joint.

13. The apparatus of claim 11 wherein the axial support member further comprises an adjustable standoff to support the limb in the proper position.

14. The apparatus of claim 5 wherein the proximal support means comprises a friction pad affixed to a backboard and a strap to hold the torso and pelvis against the friction pad.

* * * * *